United States Patent [19]
Seeberger et al.

[11] Patent Number: 6,019,048
[45] Date of Patent: Feb. 1, 2000

[54] INTERNAL MANIPULATOR FOR PIPES

[75] Inventors: Erich Seeberger, Grossenseebach; Rainer Hitzel, Roedermark, both of Germany

[73] Assignee: Siemens Aktiengesellschaft, Munich, Germany

[21] Appl. No.: 08/940,148

[22] Filed: Sep. 29, 1997

Related U.S. Application Data

[63] Continuation of application No. PCT/DE96/00541, Mar. 28, 1996.

[30] Foreign Application Priority Data

Mar. 28, 1995 [DE] Germany .......................... 195 11 310

[51] Int. Cl.$^7$ ...................................................... B61B 13/00
[52] U.S. Cl. ..................................................... 104/138.2
[58] Field of Search .............................. 104/138.1, 138.2; 346/33 P; 378/60; 73/866.5, 865.8; 33/544, 777; 15/104.05

[56] References Cited

U.S. PATENT DOCUMENTS

| | | | |
|---|---|---|---|
| 3,089,434 | 5/1963 | Anderasen | 104/138.2 |
| 3,099,227 | 7/1963 | Bryan | 104/138.2 |
| 3,775,612 | 11/1973 | Foster et al. | |
| 4,537,136 | 8/1985 | Douglas | |
| 4,601,133 | 7/1986 | Gebald et al. | |
| 4,919,223 | 4/1990 | Egger et al. | 104/138.2 |
| 5,018,451 | 5/1991 | Hapstack | 104/138.2 |
| 5,121,694 | 6/1992 | Zollinger | 104/138.2 |
| 5,749,397 | 5/1998 | Molaug | 104/138.2 |
| 5,791,255 | 8/1998 | Box | 104/138.2 |

FOREIGN PATENT DOCUMENTS

| | | |
|---|---|---|
| 3139734A1 | 4/1983 | Germany . |
| 3412519A1 | 10/1985 | Germany . |
| 4206623A1 | 9/1993 | Germany . |
| 2122 713 | 1/1984 | United Kingdom . |

*Primary Examiner*—Mark T. Le
*Attorney, Agent, or Firm*—Herbert L. Lerner; Laurence A. Greenberg

[57] ABSTRACT

An internal manipulator for pipes which has devices for treating pipe walls, the manipulator having two carriages with rolling bodies movable towards a pipe wall by antagonistically acting drives, and a rotary mounting or bogie arranged between and mounted on the carriages so as to be rotatable about a common system axis extending in a direction of travel of the manipulator, the bogie having an axially displaceable holder formed with at least one radial arm whereon at least one stop body, respectively, and one treatment unit, respectively, are arranged in a radially displaceable manner, the bogie having two radial flange plates, a rotary drive for the bogie, a servomotor of an axial drive for the holder of the treatment units, a screw spindle of the axial drive, and a guide rod for the holder having the treatment units being arranged between the flange plates so that respective axes thereof extend parallel to the system axis, the rotary drive, the servomotor, the screw spindle and the guide rod being grouped in an at least approximately equidistantly distributed manner around the system axis, the at least one radial arm of the holder extending outwardly in the direction of the pipe wall through a respective intermediate space within the group formed of the rotary drive, the servomotor, the screw spindle and the guide rod, including a stellar arrangement of simultaneously pneumatically operable stop bodies disposed in the holder in the bogie, the stop bodies, respectively, having at least one appertaining treatment unit.

13 Claims, 6 Drawing Sheets

INTERNAL MANIPULATOR FOR PIPES

CROSS-REFERENCE TO RELATED APPLICATION

This application is a continuation of application Ser. No. PCT/DE96/00541, filed Mar. 28, 1996.

BACKGROUND OF THE INVENTION

Field of the Invention

The invention relates to an internal manipulator for pipes which has devices for treating, in particular, testing pipe walls, the manipulator having two carriages provided with rolling bodies which are movable towards a pipe wall by antagonistically acting drives, and a rotary mounting or bogie which is arranged between and mounted on the carriages so as to be rotatable about a common system axis extending in the direction of travel of the manipulator, the rotary mounting or bogie having an axially displaceable holder formed with at least one radial arm whereon at least one stop body, respectively, and one treatment unit, respectively, are arranged in a radially displaceable manner, the rotary mounting or bogie having two radial flange plates, between which a rotary drive for the rotary mounting or bogie, a servomotor of an axial drive for the holder of the treatment units, a screw spindle of the axial drive, and a guide rod for the holder having the treatment units are arranged so that the axes thereof extend parallel to the system axis.

Such manipulators serve to treat pipelines which are inaccessible, whether for spatial reasons or due to heat, pressure and radiation. Manipulators of this type may be constructed to be self-propelled, but they may also be pulled or pushed and be part of a series arrangement of a whole group of pipe vehicles. The expression "treatment" refers to all operations which are concerned with the condition of the pipeline to be negotiated or traversed, whether this is an inspection wherein the actual visual condition is being recorded, an ultrasonic examination of welds, mechanical treatment operations such as welding or grinding, or coating operations by which, for example, the inner wall of a respective pipe is to be provided with a protective coating. Particularly in reactor construction, extremely stringent requirements which the function of such an internal manipulator for pipes must satisfy are imposed upon the condition of pipelines and on the documentation of this condition.

The published German Patent Document DE 34 12 519 C2 discloses an internal manipulator for pipes which is of the general type mentioned at the introduction hereto, wherein the rotary drive for the rotary mounting or bogie, the servomotor of the axial drive for the holder of the treatment units, the screw spindle of the axial drive, and a guide rod for the holder with the treatment units are accommodated inside a quadrant of the cross-sectional are of the manipulator. In this regard, the supporting body of the rotary mounting or bogie is formed of a hollow half-cylinder wherein a holder is accommodated, a single radial arm having a stop body and a total of eight treatment units being fastened to the holder. In this case, the holder with the treatment units fills essentially two further quadrants of the manipulator cross section. The conventional construction or solution is preferred for negotiating or traversing pipelines having an inside diameter of more than 200 mm.

In connection with increasing safety requirements, it has become necessary to develop internal manipulators of pipes which are also used in conjunction with smaller pipeline diameters, for example, down to about 80 mm inside diameter.

SUMMARY OF THE INVENTION

It is accordingly an object of the invention to provide an internal manipulator for pipes which is of the general type described at the introduction hereto and which permits further miniaturization and is usable, preferably, but not exclusively, for pipelines having an inside diameter of less than 200 mm, preferably less than 120 mm.

With the foregoing and other objects in view, there is provided, in accordance with the invention, an internal manipulator for pipes which has devices for treating pipe walls, the manipulator having two carriages with rolling bodies movable towards a pipe wall by antagonistically acting drives, and a rotary mounting or bogie arranged between and mounted on the carriages so as to be rotatable about a common system axis extending in a direction of travel of the manipulator, the bogie having an axially displaceable holder formed with at least one radial arm whereon at least one stop body, respectively, and one treatment unit, respectively, are arranged in a radially displaceable manner, the bogie having two radial flange plates, a rotary drive for the bogie, a servomotor of an axial drive for the holder of the treatment units, a screw spindle of the axial drive, and a guide rod for the holder having the treatment units being arranged between the flange plates so that respective axes thereof extend parallel to the system axis, the rotary drive, the servomotor, the screw spindle and the guide rod being grouped in an at least approximately equidistantly distributed manner around the system axis, the at least one radial arm of the holder extending outwardly in the direction of the pipe wall through a respective intermediate space within the group formed of the rotary drive, the servomotor, the screw spindle and the guide rod, including a stellar arrangement of simultaneously pneumatically operable stop bodies disposed in the holder in the bogie, the stop bodies, respectively, having at least one appertaining treatment unit.

In accordance with another feature of the invention, the axes of the rotary drive, the servomotor, the screw spindle and the guide rod lie at least approximately at respective corner points of an imaginary square having diagonals intersecting at the system axis, and the holder has four radial arms arranged in an alternating manner with the rotary drive, the servomotor, the screw spindle and the guide rod and, respectively, having at least one radial pneumatic drive by which a respective stop body and a respective treatment unit is movable up to the pipe wall so that at least four treatment elements and four stop bodies constantly bear against the inner wall of the respective pipe during a treatment phase.

In accordance with a further feature of the invention, radial feed forces of the drives of the rolling bodies of the carriages, on the one hand, and actuating forces of the stop bodies at the bogie, on the other hand, are matched to one another in terms of design so that the position of the system axis inside a pipe bend extends at least approximately tangentially to the bend axis.

In accordance with an added feature of the invention, the internal manipulator for pipes includes adjustable end stops on the carriages for adjusting the feed forces of the rolling bodies.

In accordance with an additional feature of the invention, the internal manipulator for pipes includes pressure limiters disposed in the pneumatic system for adjusting the feed forces of the stop bodies on the bogie.

In accordance with yet another feature of the invention, the pneumatic drives for the stop bodies and the treatment units have a stroke of such dimension that the limit positions of the stop bodies lie inside and outside the nominal diameter of the respective pipe to be traversed.

In accordance with yet a further feature of the invention, the rotary drive for the bogie is active via a pinion on a toothed rim arranged on one of the carriages.

In accordance with yet an added feature of the invention, the servomotor of the axial drive is in cooperative engagement with the screw spindle of the axial drive via a toothed belt extending in the form of a curved loop around part of the periphery of the toothed rim between the respective carriage and the bogie.

In accordance with yet an additional feature of the invention, the treatment units are, at least in part, ultrasonic probes.

In accordance with another feature of the invention, at least one of the treatment units is a position transmitter for a position receiver arranged outside the respective pipe.

In accordance with a further feature of the invention, at least one displacement gauge is allocated to one of the carriages.

In accordance with an added feature of the invention, at least one of the treatment units is a welding unit.

In accordance with a concomitant feature of the invention, at least one of the treatment units is a grinding unit.

In the case of the internal manipulator for pipes described hereinbefore, the rotary drive, the servomotor, the screw spindle and the guide rod are grouped in an at least approximately equidistantly distributed manner around the system axis, and at least one radial arm of the holder is guided outwardly in the direction of the pipe wall in each case through one of a plurality of intermediate spaces inside the group which is made up of the rotary drive, the servomotor, the screw spindle and the guide rod.

Due to the design specification according to the invention, an exceptionally high "packing density" of the drive and guide devices belonging to the rotary mounting or bogie is achieved, i.e., the enveloping surface which can be imagined as being placed around such a manipulator is filled to an exceptionally large degree with functional parts. The requisite "travel profile" can thereby be further reduced to a noticeable extent without jeopardizing the function of the entire device.

Furthermore, it is especially advantageous in connection with a further development of the invention if the holder in the bogie has a stellar or star-shaped arrangement of simultaneously pneumatically operable stop bodies having at least one appertaining treatment unit each.

This measure enables the number of treatment units to be increased in accordance with the number of arms, so that a multiplicity of different treatment and/or test methods are possible at the same time.

An especially space-saving arrangement is achieved in connection with yet again a further development of the invention in that the axes of the rotary drive, the servomotor, the screw spindle and the guide rod lie at least approximately at the corner points of an imaginary square, the diagonals of which intersect at the system axis, and in that the holder has four radial arms which are arranged in an alternating manner with the rotary drive, the servomotor, the screw spindle and the guide rod and in each case have at least one radial pneumatic drive, by which a stop body and a treatment unit can be moved up to the pipe wall so that at least four treatment elements and four stop bodies constantly bear against the inner wall of the pipe during the treatment phase.

Whereas it was only possible, as a rule, to treat rectilinear pipe sections with the hitherto known internal manipulator, it is also possible, with an internal manipulator further developed in accordance with the invention, to treat the inner surfaces of pipe bends, namely when the radial feed forces of the drives of the rolling bodies of the carriages, on the one hand, and the actuating forces of the stop bodies at the rotary mounting or bogie, on the other hand, are matched to one another in terms of design so that the position of the system axis inside a pipe bend extends at least approximately tangentially to the bend axis.

The following explanation will serve to clarify this action: normally, the rolling bodies of the carriages determine the spatial position of the system axis inside the bend, i.e., the system axis forms a chord or secant relative to the bend axis, the intersecting points lying in the region of the two carriages. The result thereof is that the holder's axis of rotation which certainly coincides with the system axis, extends in a considerably eccentric manner relative to the bend cross section. In the normal condition, the holder is located approximately in the center between both carriages. Because the holder rotates with the treatment units during the treatment, considerable amplitudes of motion result in the region of the stop bodies, which of course have to be absorbed by the pneumatic drive system. On the other hand, however, the different radii of motion produce, in return, different peripheral velocities which, if possible, should not occur. The construction measures according to the invention, by which the system axis is brought into at least the greatest possible proximity to the tangent to the bend axis, achieve the effect that the axis of rotation of the holder and the bend axis essentially coincide, so that the aforedescribed problems do not occur.

The aforedescribed tangential adjustment of the system axis relative to the bend axis can be achieved in an especially simple manner by providing adjustable end stops on the carriages for adjusting the feed forces of the rolling bodies. The feed forces become zero when the end stops are reached. In this case, it is merely necessary to know the spatial position and the radius of curvature of the relevant bend in order to be able appropriately to pre-adjust the end stops on the carriages. Furthermore, by an adjustment of the feed forces of the stop bodies on the rotary mounting or bogie by pressure limiters in the pneumatic system, a certain force relationship is imposed, i.e, by the pressure limiters in the pneumatic system having an appropriately high setting, the holder rotating about the system axis has a centering effect on the pipeline cross section present at this location, as a result of which the centricity is further improved. Other features which are considered as characteristic for the invention are set forth in the appended claims.

Although the invention is illustrated and described herein as embodied in an internal manipulator for pipes, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, wherein:

DESCRIPTION OF THE PREFERRED EMBODIMENTS

Figure 1:
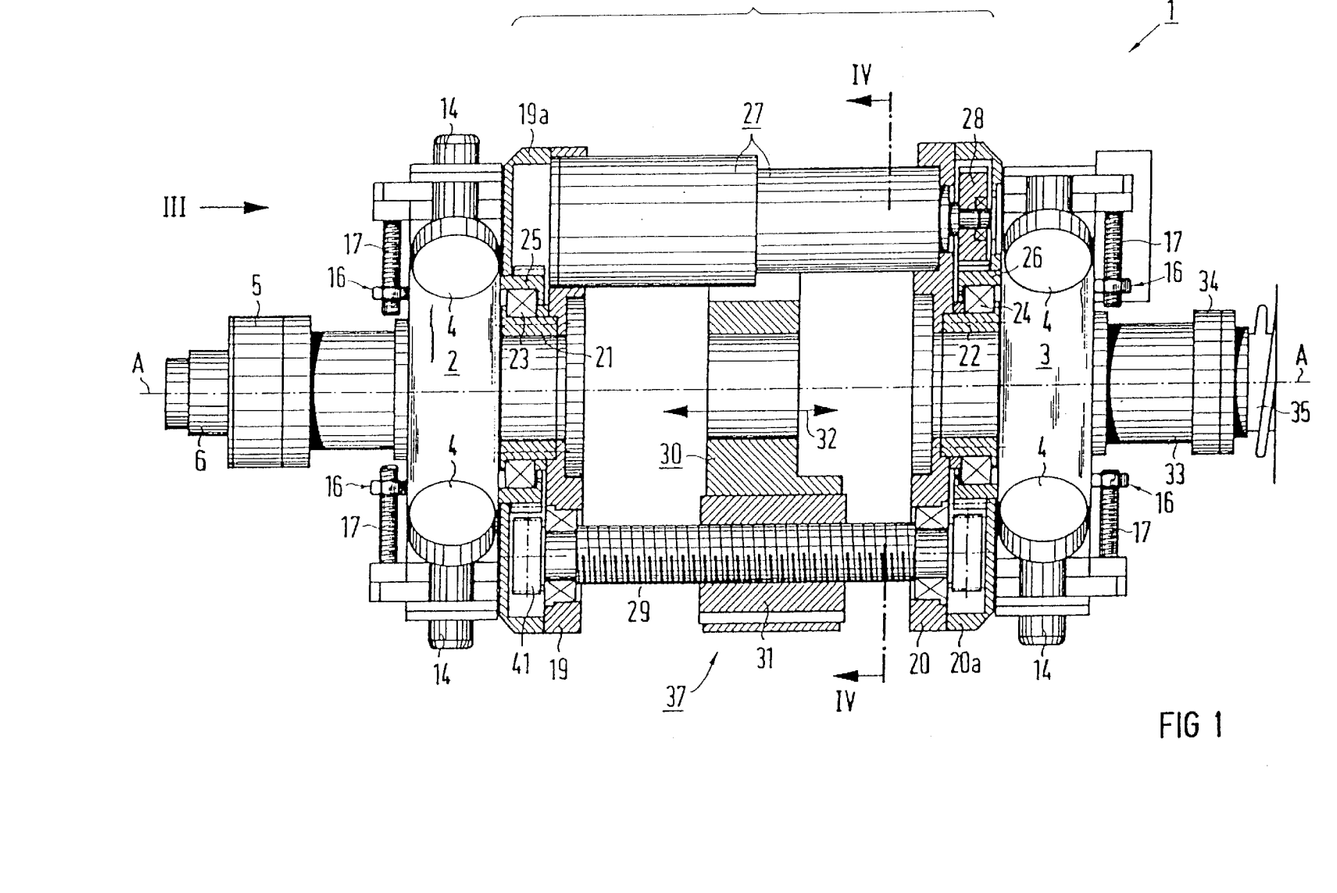
FIG. 1 is a side elevational view of the two carriages of the internal manipulator for pipes according to the invention showing the rotary mounting or bogie in a partial axial sectional view taken along the line I—I in FIG. 4.

Referring now to the drawings and, first, particularly to FIG. 1 thereof, there is shown therein a treatment part of an internal manipulator 1 for pipes, including two carriages 2 and 3, respectively, equipped with four rolling bodies 4 constructed in the form of rubber-tired wheels in the illustrated embodiment. The carriage 2 at the front of the manipulator 1 is equipped with a television camera 5 having optics 6 which are oriented coaxially to the travel path of the manipulator 1.

Figure 3:
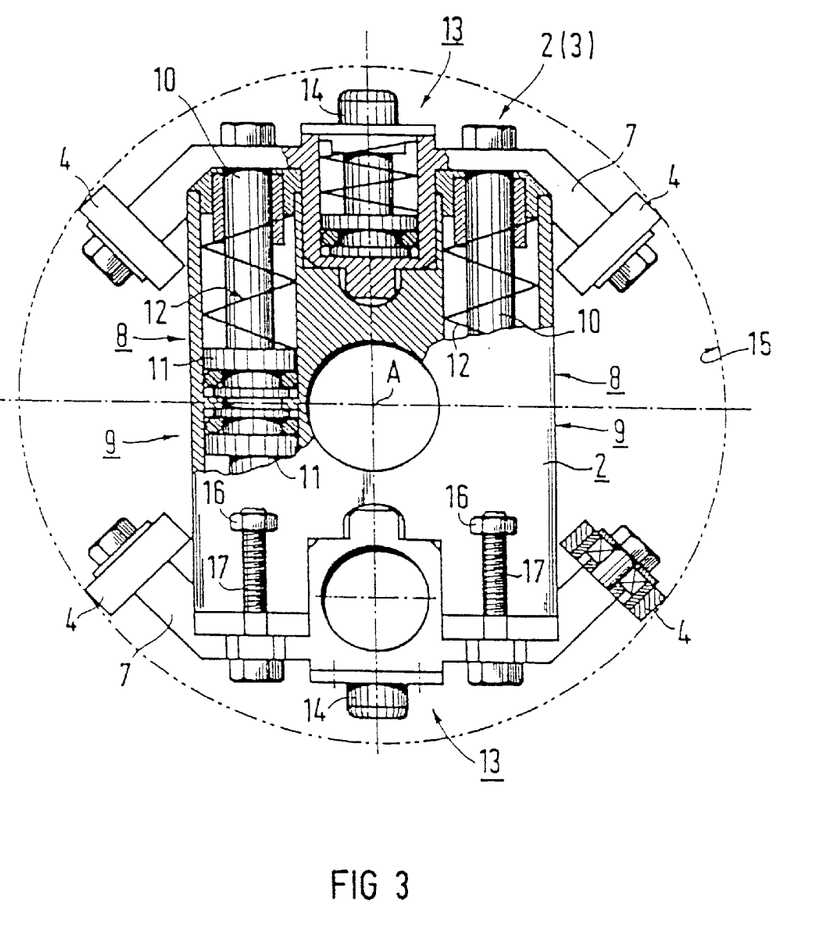
FIG. 3 is a fragmentary front elevational view, partly broken away and in section, of one of the carriages as seen in the direction of arrow III in FIG. 1.

As is apparent from FIG. 3, the respective carriages 2 and 3 have two angle-shaped yokes 7 disposed in a mirror-image arrangement, the rolling bodies 4 being fastened to the ends of the yokes 7. The yokes 7 are provided with drives 8 and 9, which act antagonistically, i.e., in opposition to one another and are constructed as pneumatic drives, respectively, having two parallel piston rods 10 with pistons 11. The pistons 11 are held by restoring springs 12 in a pressureless condition in the illustrated retracted position.

Each of the two yokes 7 has, in the respective center thereof, an arresting device 13 with a locking pin 14 which is fastened to a piston which is not otherwise shown in detail. An application of pressure to the two pistons enables the two locking pins 14 to be pressed against the inner pipe wall 15, so that the respective carriage 2,3 and, consequently, the manipulator 1 are fixed in position. The rolling bodies 4 are likewise pressed against the pipe wall 15 by the drives 8 and 9, thereby preventing undesirable rotation about the system axis A—A.

The movement causing an extension of the piston rods 10 and thus of the rolling bodies 4 is limited by adjustable end stops 16 which are formed by nuts on screws 17 which extend parallel to the piston rods 10. Appropriate preadjustment of the end stops 16 enables the system axis A—A to extend eccentrically to the axis of the pipe bend in the region of the carriages 2 and 3 but tangentially to the bend axis in the region of the holder which is described in greater detail hereinbelow.

Pneumatic lines and boreholes are not shown in FIG. 3 in the interest of simplicity; however, the locations thereof are readily apparent from the functions which are specified.

Figure 2:
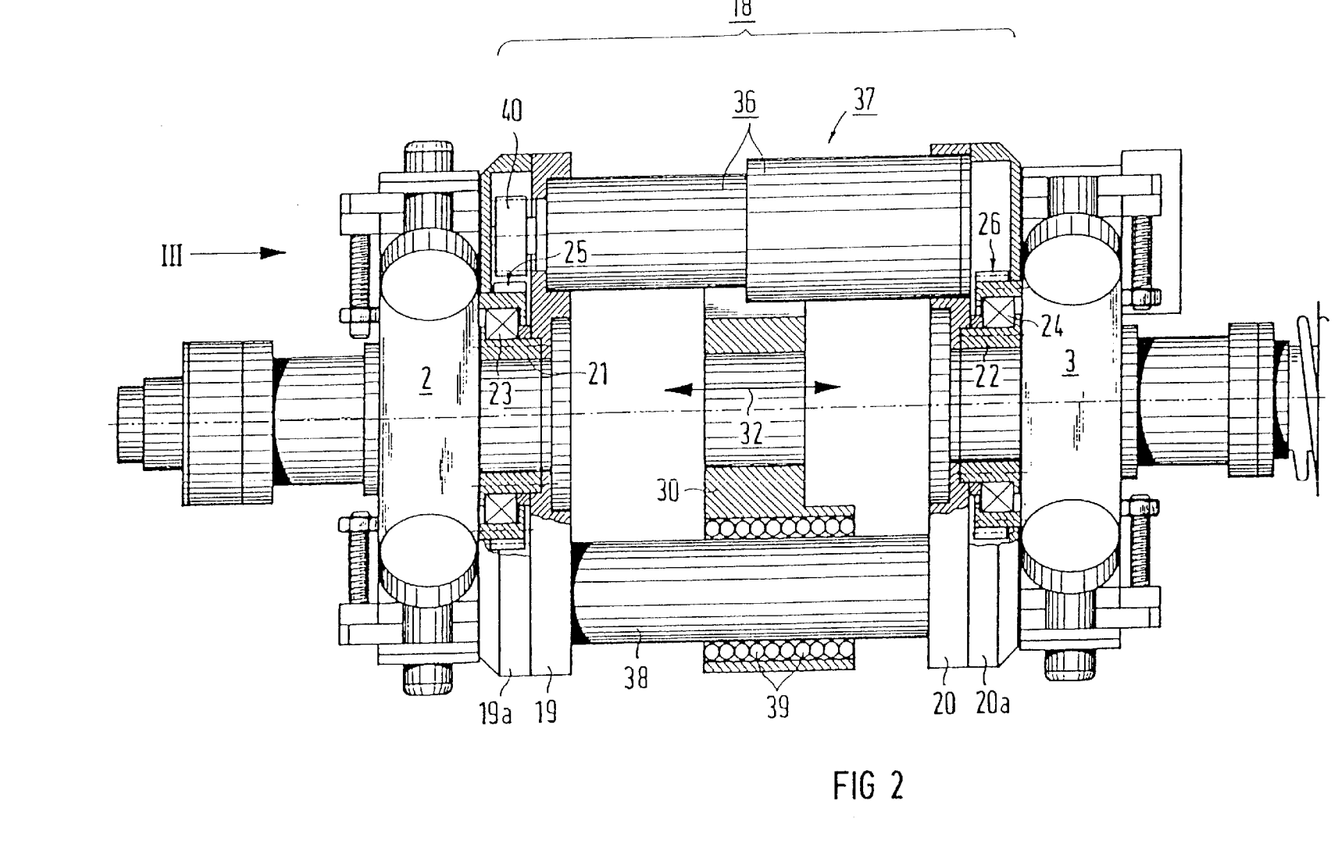
FIG. 2 is also a side elevational view of the two carriages, like that of FIG. 1 but with the rotary mounting or bogie rotated through 90°, in accordance with a partial axial sectional view taken along the line II—II in FIG. 4.

According to FIGS. 1 and 2, a rotary mounting or bogie 18 having two radial flange plates 19 and 20 is located between the carriages 2 and 3. Respective bearing rings 21 and 22, each carrying a respective anti-friction bearing 23, 24 at the outer periphery thereof, is in each case screwed to the flange plates 19 and 20. The anti-friction bearings 23 and 24, respectively, are in turn accommodated in each case in respective toothed rims 25 and 26, which are screwed to the carriage 2, on the one hand, and the carriage 3, on the other hand. Consequently, between the two carriages 2 and 3 and the rotary mounting or bogie 18, two rotary bearings concentric to the system axis A—A are formed for the rotary mounting or bogie 18.

According to FIG. 1, initially a rotary drive 27 in the form of a geared motor having an output shaft cooperating with the toothed rim 26 on the carriage 3 via a pinion 28 extends between the two flange plates 19 and 20. By appropriate activation of the rotary drive 27, the rotary mounting or bogie 18 can be forced to assume a quite definite spatial position relative to the two carriages 2 and 3.

Furthermore, a screw spindle 29 journalled at both ends thereof and driven in a manner described in greater detail hereinbelow is located between the two flange plates 19 and 20. This screw spindle 29 serves to displace in axial direction a holder 30 only partly shown in FIG. 1 which has a spindle nut 31 constructed as a recirculating ball nut, the details of which are not shown here in the interest of simplicity. The holder 30 is movable in the direction of the double arrow 32 relative to the rotary mounting or bogie 18 by rotating the screw spindle 29 so that, for example, the regions on both sides of a weld can be examined in this manner one after the other by ultrasonic testing. The flange plates 19 and 20 are covered by congruent caps 19a and 20a on the sides thereof facing towards the toothed rims 25 and 26 and the anti-friction bearings 23 and 24.

The carriage 3 at the rear of the manipulator 1, as shown in Fig, 1, for example, is provided with a pipe connection 33 which is attached via a flange connection 34 to a bellows 35 forming a connection with a following pipe vehicle, which is constructed, for example, as a drive vehicle. Such bellows 35 permit high flexibility and thus good curve-negotiation or traversal ability of a whole system of internal manipulators for pipes or pipelines.

FIG. 2 presents a view of the carriages 2 and 3 like that of FIG. 1, but the rotary mounting or bogie 18 is rotated through 90° relative to the location thereof in FIG. 1. In this case, the servomotor 36 of an axial drive 37, to which the screw spindle 29 according to FIG. 1 also belongs, lies in a sectional plane taken along the line II—II in FIG. 4. This servomotor 36 is also constructed as a geared motor and is fastened between the flange plates 19 and 20. Arranged so as to lie diametrically opposite the servomotor 36 is a guide rod 38 which is likewise fastened between the flange plates 19 and 20, the holder 30 being guided thereon by a ball sleeve 39. The servomotor 36 of the axial drive 37 has a toothed disk 40 which cooperates with a further toothed disk 41 in a manner shown in FIG. 8, the further toothed disk 41 being located at the front end of the screw spindle 29, as viewed in FIG. 1.

Figure 8:
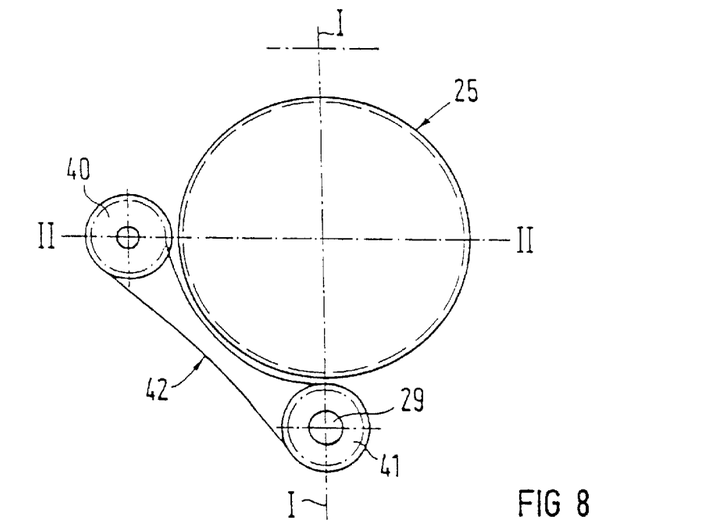
FIG. 8 is a diagrammatic representation of a belt drive between a servomotor of an axial drive and a screw spindle thereof as viewed in FIG. 1.

The toothed disks 40 and 41 are connected to one another by a toothed belt 42, one strand of which extends in a curved manner around the front toothed rim 25, as shown in FIG. 8. In this manner, an especially space-saving arrangement is attained.

Figure 4:
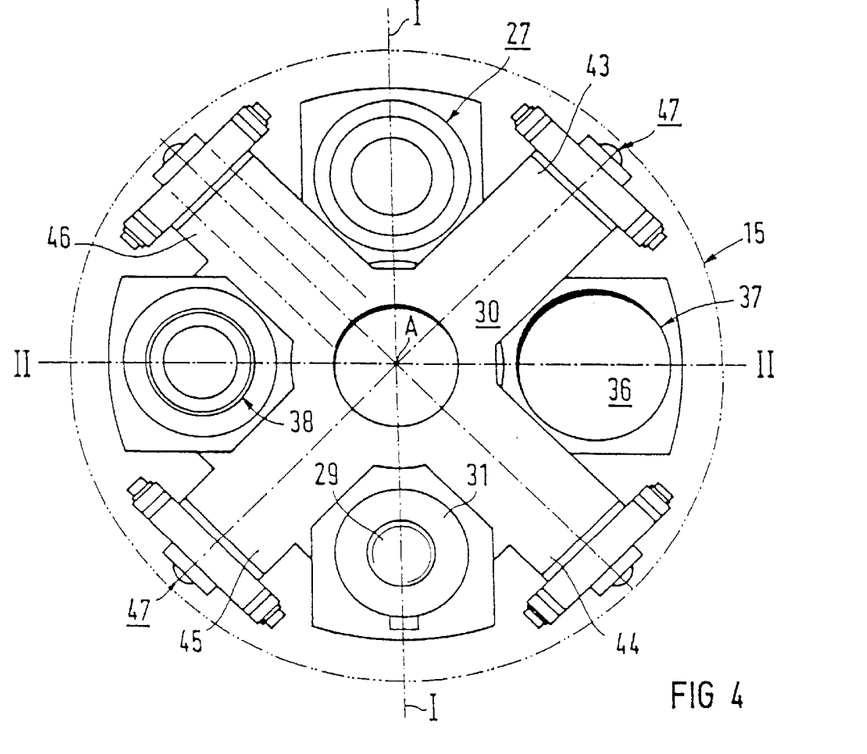
FIG. 4 is a partial section view of FIG. 1 taken along the line IV—IV, in the direction of the arrows.

FIG. 4 shows that the holder 30 is of stellar design and has four arms 43, 44, 45 and 46, of which each is provided with at least one pneumatically operable stop body 47 displaceable towards the pipe wall 15.

Readily apparent from FIG. 4 is that the axes of the rotary drive 27, the servomotor 36, the screw spindle 29 and the guide rod 38 are arranged at the corner points of an imaginary square, the diagonals of which intersect at the system axis A—A. The four radial arms 43 to 46 of the holder 30 are arranged in an alternating manner with the axes of the rotary drive 27, the servomotor 36, the screw spindle 29 and the guide rod 38 and have, respectively, at least one radial pneumatic drive, which will be explained in greater detail with reference to FIG. 5.

Figure 5:
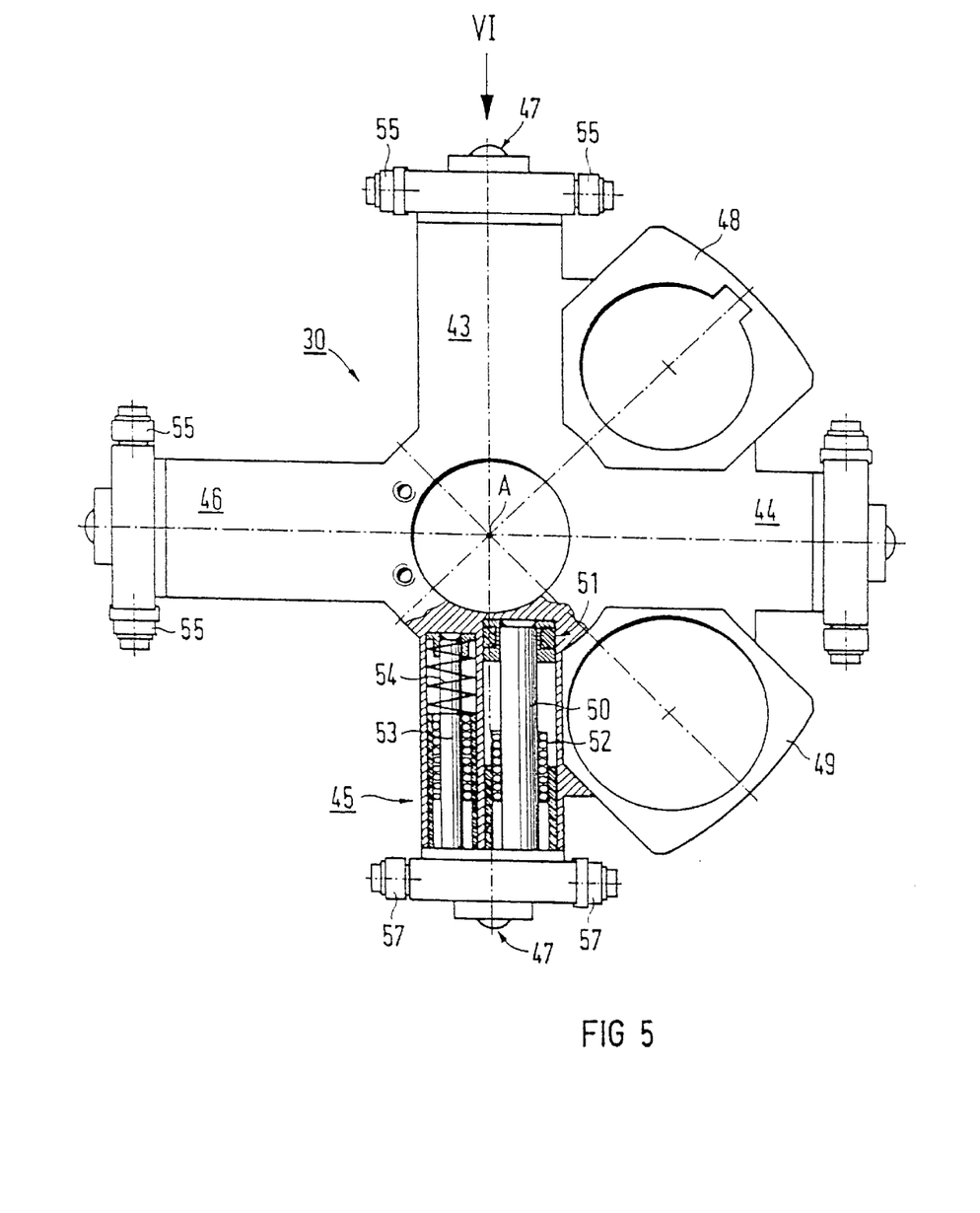
FIG. 5 is an enlarged view of FIG. 4, displaying the holder in greater detail, one of the four arms thereof being shown in section taken along the line V—V with a view thereof in the direction of the arrow V in FIG. 6.

It is apparent from FIG. 5 that the holder 30, as far as its basic concept is concerned, is of star-shaped or cruciform design and has the already previously described arms 43 to 46. A lug 48 for accommodating the spindle nut 31 (FIGS. 1 and 4) is located between the arms 43 and 44, and a hollow guide body 49 for accommodating the guide rod 38 is located between the arms 44 and 45. FIG. 5 also shows the extremely compact spatially and particularly torsionally rigid design of all the movable elements of the manipulator 1. In FIG. 5, only the arm 45 is shown in a sectional view, although this representation also serves to represent the other arms 43, 44 and 46. Each of the stop bodies 47 is connected to a piston 51 via a piston rod 50 and is guided in a ball sleeve 52. In order to prevent rotation of the stop body 47 and the treatment unit connected thereto, a guide rod 53 is arranged parallel to the piston rod 50, the guide rod 53 being likewise guided in a ball sleeve and being under the action of a restoring spring 54. The instant at which compressed air has been applied to all of the pistons 51, the stop bodies 47 are brought to bear against the inner wall 15 of the respective pipe, resulting in a centering effect being produced on the holder 30, indeed, a centering with regard to the system axis A—A.

Figure 6:
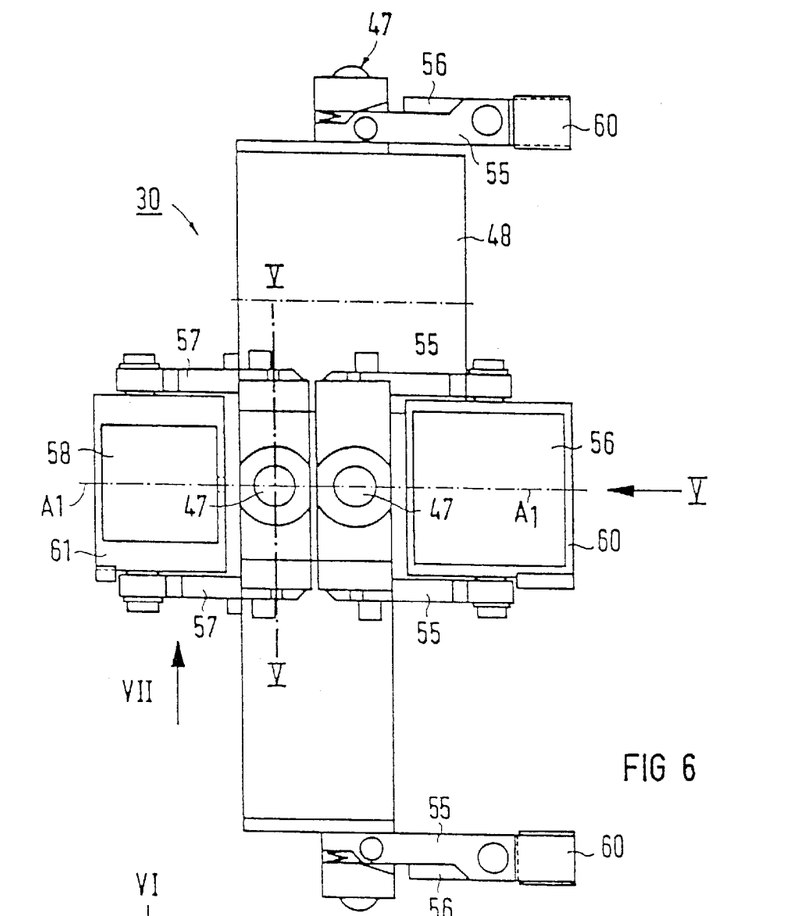
FIG. 6 is a plan view of the holder as seen in the direction of the arrows VI in FIGS. 5 and 7, i.e., rotated through 90° relative to FIG. 5.
Figure 7:
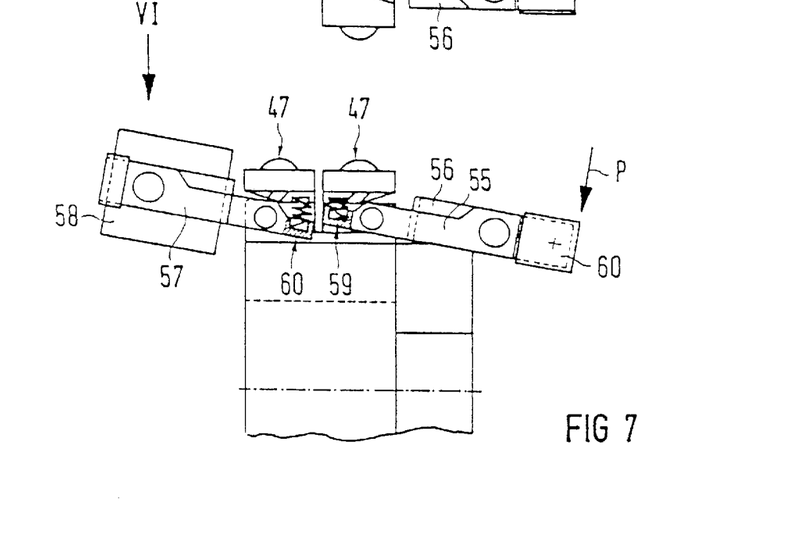
FIG. 7 is a fragmentary side elevational view of FIG. 6 as seen in the direction of the arrow VII.

FIGS. 6 and 7 show that in each case two stop bodies 47 are arranged in the direction of the system axis A—A in each of the arms 43 to 46. In FIG. 5, therefore, a pneumatic drive and a guide unit have to be imagined as being arranged lying one behind the other in each of the arms. A treatment unit 56 is allocated to each of these stop bodies 47 via two articulated levers 55, the treatment unit 56 in the illustrated embodiment being formed of an ultrasonic probe with a transmitter and a receiver, so that in this manner the condition of the pipe wall can be examined, in particular, the quality of welds provided therein. Such treatment units are state of the art, so that this need not be dealt with in any greater detail herein. A holder 30 according to FIG. 6 is provided with a total of four treatment units 56 on the periphery, the treatment units 56 being bringable one after the other into cooperation with the pipe wall by continuous rotation of the holder 30. The measuring signals obtained in the process are logged or recorded and serve to verify the satisfactory condition of the pipe wall, in particular, the welds applied therein.

On the opposite side, one of the stop bodies 47 is connected via two articulated levers 57 to a position transmitter 58 which cooperates with a position receiver which is arranged outside the pipe and is not shown in the figures. It is apparent from FIG. 7 that the articulated levers 55 and 57 are under the action of compression springs 59 and 60, by which the treatment units 56 and the position transmitter 58 are swung radially outwardly, i.e., in front of the stop bodies 47. Because the articulated levers 55, respectively, have two parallel axes, the treatment units 56 and the position transmitter 58 can be brought to bear fully against the pipe wall. In FIG. 7, at the right-hand side thereof, there is clearly shown what happens if an external force P acts upon the treatment unit 56: the compression spring 59 is compressed and the treatment unit 56 can move inwardly out of the way. Such a condition occurs, for example, if the manipulator passes through a pipe bend. In the interest of completeness, it may also be mentioned that the treatment units 56 and the position transmitter 58 are arranged inside frames 60 and 61, respectively, and are pivotable in these frames about further axes A1, so that a cardanic suspension is assured.

We claim:

1. An internal manipulator for entry into pipes and for testing and/or conditioning pipe walls, comprising:

two carriages disposed remote from one another and defining a system axis therebetween, each of said carriages including rolling bodies and antagonistically acting drives for moving said rolling bodies toward a pipe wall; and a rotary mounting or bogie disposed between said carriages and mounted to said carriages for rotation about the system axis, said rotary mounting including:

a holder displaceable along the system axis, said holder having a stellar arrangement of radial arms extending away from the system axis, each one of said radial arms having a pneumatically extendable stop body thereby defining a plurality of stop bodies, said plurality of stop bodies being simultaneously extendable towards the pipe wall;

two radial flange plates;

a rotary drive disposed between said two radial flange plates for rotating said rotary mounting about the system axis;

an axial drive having a servomotor disposed between said two radial flange plates;

a screw spindle disposed between said two radial flange plates and cooperating with said servomotor for displacing said holder along the system axis; and a guide rod disposed between said two radial flange plates for guiding said holder along the system axis;

said rotary drive, said servomotor, said screw spindle, and said guide rod being disposed parallel to the system axis, disposed approximately equidistant from the system axis, and forming intermediate spaces therebetween, each one of said radial arms extending through one of the intermediate spaces.

2. The internal manipulator for pipes according to claim 1, wherein:

each one of said plurality of stop bodies has a device selected from the group consisting of a testing unit for testing the pipe wall and a conditioning unit for conditioning the pipe wall;

each of said servomotor, said screw spindle, and said guide rod has an axis that lies at least approximately at a respective corner point of an imaginary square having diagonals intersecting at the system axis, and said stellar arrangement of radial arms includes four radial arms, each one of said radial arms includes a pneumatic drive for extending said stop body and said device to the pipe wall.

3. The internal manipulator for pipes according to claim 1, wherein said antagonistically acting drives provide feed forces to radially move said rolling bodies toward the pipe wall, and said plurality of stop bodies include pneumatic drives with matched actuating forces so that a position of the system axis inside a curved section of a pipe extends at least approximately tangentially to a curved axis of the pipe.

4. The internal manipulator for pipes according to claim 3, including adjustable end stops on the carriages for adjusting the feed forces of the rolling bodies.

5. The internal manipulator for pipes according to claim 3, including pressure limiters disposed in said pneumatic drives for adjusting the actuating forces of said plurality of stop bodies on said bogie.

6. The internal manipulator for pipes according to claim 3, wherein said pneumatic drives for said plurality of stop bodies have a stroke of such dimension that a limit position of each one of said plurality of stop bodies lies inside and outside a nominal diameter of the pipe to be traversed.

7. The internal manipulator of pipes according to claim 1, wherein the rotary drive for the bogie is active via a pinion on a toothed rim arranged on one of the carriages.

8. The internal manipulator for pipes according to claim 1, including a toothed rim disposed between said bogie and one of said carriages, and a toothed belt extending around said toothed rim and said screw spindle, said toothed rim engaging said servomotor.

9. The internal manipulator for pipes according to claim 1, wherein said device of at least one of said plurality of stop bodies is an ultrasonic probe.

10. The internal manipulator for pipes according to claim 1, wherein said device of at least one of said plurality of stop bodies is a position transmitter for a position receiver arranged outside of a pipe.

11. The internal manipulator for pipes according to claim 1, wherein at least one displacement gauge is allocated to one of the cariages.

12. The internal manipulator for pipes according to claim 1, wherein said device of at least one of said plurality of stop bodies is a welding unit.

13. The internal manipulator for pipes according to claim 1, wherein said device of at least one of said plurality of stop bodies is a grinding unit.

* * * * *